(12) United States Patent
Liu (10) Patent No.: US 10,935,513 B2
(45) Date of Patent: Mar. 2, 2021

(54) SENSOR FOR VOLATILE ORGANIC COMPOUND DETECTION

(71) Applicant: CASE WESTERN RESERVE UNIVERSITY, Cleveland, OH (US)

(72) Inventor: Chung Chiun Liu, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 138 days.

(21) Appl. No.: 15/512,813

(22) PCT Filed: Sep. 18, 2015

(86) PCT No.: PCT/US2015/050917
§ 371 (c)(1),
(2) Date: Mar. 20, 2017

(87) PCT Pub. No.: WO2016/044711
PCT Pub. Date: Mar. 24, 2016

(65) Prior Publication Data
US 2017/0248541 A1    Aug. 31, 2017

Related U.S. Application Data

(60) Provisional application No. 62/052,214, filed on Sep. 18, 2014.

(51) Int. Cl.
*G01N 27/407* (2006.01)
*G01N 33/487* (2006.01)
(Continued)

(52) U.S. Cl.
CPC ..... *G01N 27/4074* (2013.01); *G01N 27/4045* (2013.01); *G01N 27/48* (2013.01);
(Continued)

(58) Field of Classification Search
None
See application file for complete search history.

(56) References Cited

U.S. PATENT DOCUMENTS 4,563,249 A    1/1986 Hale
4,571,292 A    2/1986 Liu et al.
(Continued)

FOREIGN PATENT DOCUMENTS

EP    0221381 A2    5/1987
EP    2506001 A1    10/2012
WO    2008/073167 A1    6/2008

OTHER PUBLICATIONS

Hicks et al. (Sensors and Actuators B 194, 283-289, Jan. 13, 2018 NPL, 8 pages) (Year: 2014).*
(Continued)

*Primary Examiner* — J. Christopher Ball
(74) *Attorney, Agent, or Firm* — Tarolli, Sundheim, Covell & Tummino LLP (57) ABSTRACT

A sensor for detecting volatile organic compounds (VOCs) includes a substrate, a working electrode formed on a surface of the substrate, a counter electrode formed on the surface of the substrate, a dielectric layer covering a portion of the working electrode and counter electrode and defining an aperture exposing other portions of the working electrode and counter electrode.

16 Claims, 3 Drawing Sheets

(51) Int. Cl.
| | |
|---|---|
| *G01N 27/404* | (2006.01) |
| *G01N 27/48* | (2006.01) |
| *G01N 33/00* | (2006.01) |
| *G01N 33/497* | (2006.01) |

(52) U.S. Cl.
CPC ... *G01N 33/0047* (2013.01); *G01N 33/48707* (2013.01); *G01N 33/497* (2013.01); *G01N 2033/4975* (2013.01)

(56) References Cited

U.S. PATENT DOCUMENTS

| | | | | |
|---|---|---|---|---|
| 4,795,533 | A  * | 1/1989 | Young | G01N 27/4074 |
| | | | | 204/421 |
| 7,258,773 | B2 | 8/2007 | Zhou et al. | |
| 2004/0129565 | A1 * | 7/2004 | Prohaska | G01N 27/4074 |
| | | | | 204/424 |
| 2006/0266642 | A1 * | 11/2006 | Akle | F03G 7/005 |
| | | | | 204/282 |
| 2007/0191499 | A1 * | 8/2007 | Chmelka | B01D 67/0048 |
| | | | | 521/27 |
| 2008/0027135 | A1 | 1/2008 | Sondek et al. | |
| 2010/0116691 | A1 | 5/2010 | Papadimitrakopoulos et al. | |
| 2012/0046181 | A1 | 2/2012 | Harb et al. | |
| 2013/0153442 | A1 | 6/2013 | Chen et al. | |
| 2014/0083864 | A1 * | 3/2014 | Rowhani | G01N 27/4045 |
| | | | | 205/778.5 |

OTHER PUBLICATIONS

Bard and Faulkner (Electrochemical Methods: Fundamentals and Applications, John Wiley and Sons, (Year: 1980).*
Madasamy et al. (Talanta, 100, 168-174) (Year: 2012).*
Pospisil, Experimental Techniques in Bioelectrochemistry (Year: 1996).*
Shao, et al. "Tungsten Trioxide Hydrate Incorporated Nafion Composite Membrane for Proton Exchange Membrane Fuel Cells Operated above 100 ° C.", Chemical Engineering Communications, 194(5): p. 667-674, Jan. 2007.*
Shen, et al., "An iridium nanoparticles dispersed carbon based thick film electrochemical biosensor and its application for a single use, disposable glucose biosensor", Sensors and Actuators B, vol. 125 (2007) pp. 106-113.
Supplemental European Search Report for Application No. 15841626.3-1003/3194946.
Hicks, et al., "Electrochemical impedance characterisation of tungsten trioxide-polyaniline nanocon1posites for room temperature acetone sensing", Sensors and Actuators, 2014, pp. 283-289.
Extended European Search Report for Application No. 15841626.3-1003/3194946.
Office action for Chinese Patent Application No. 2015800566479, dated Sep. 17, 2018.
Shao, ZG, et al., "Tungsten Trioxide Hydrate Incorporated Nation Composite Membrane for Proton Exchange Membrane Fuel Cells Operated Above 100° C.", 2007, Chemical Engineering Communications, 194:667-674.
Park, IS, et al., "Fabrication of catalyst-coated membrane-electrode assemblies by doctor blade method and their performance in fuel cells", Oct. 15, 2010, Journal of Power Sources, vol. 195, Issue 20, pp. 7078-7082.
Verbrugge MW, et al., "Experimental and theoretical investigation of perfluorosulfonic acid membranes equilibrated with aqueous sulfuric acid solutions", Nov. 1988, Journal of Physical Chemistry, vol. 92, No. 23, pp. 6778-6783.
Office action for Chinese Patent Application No. 2015800566479, dated Nov. 1, 2019.
Q. Xue, et al. "An integrated micro immunosensor for hemoglobin-A1c level detection", In Pr5oceedings of 2010 IEEE/ASME International Conference on Mechatronic and Embedded Systems and Applications, p. 208-212, Jul. 2010.
First Named Inventor: Chung Chiun Liu; Title: System and Methods for the Detection of Biomarkers of Neurodegenerative Disorders; U.S. Appl. No. 15/970,738, filed May 3, 2018; Final Office Action; Notification dated Sep. 22, 2020.
First Named Inventor: Chung Chiun Liu; Title: System and Methods for the Detection of HBA1C; U.S. Appl. No. 15/973,218, filed May 7, 2018; Final Office Action; Notification dated Sep. 1, 2020.
First Named Inventor: Chung Chiun Liu; Title: System and Method for Detecting Lysyl Oxidase-Like 2 Protein (LOXL2) and Breast Cancer; U.S. Appl. No. 16/168,630, filed Oct. 23, 2018; Office Action; Notification dated Sep. 21, 2020; 7 pgs.
First Named Inventor: Chung Chiun Liu; Title: System and Methods for the Detection of Biomarkers of Glypican-1; U.S. Appl. No. 16/118,216, filed Aug. 30, 2018; Final Office Action; Notification dated Oct. 8, 2020.
Karalemas et al., Talanta, 2000, 53:391-402.
Moreno-Bueno, et al., EMBO Mol Med., 2011, 3:528-544.

* cited by examiner

SENSOR FOR VOLATILE ORGANIC COMPOUND DETECTION

RELATED APPLICATION

This application claims priority from U.S. Provisional Application No. 62/052,214, filed Sep. 18, 2014, the subject matter of which is incorporated herein by reference in its entirety.

BACKGROUND

The ability to diagnose and characterize a disease through the gaseous emissions of volatile organic compounds (VOCs) from a patient is becoming increasingly recognized in medicine. Technical studies have shown that it is possible to detect, amongst others, melanoma, lung cancers, eye infections, brain cancers, schizophrenia, diabetes, wound infections, urinary tract infections and MRSA, from the gaseous emissions emanating from patient's blood, sweat, breath, urine and fecal samples.

For example, abnormal concentrations of the breath VOCs are reported to correlate with unhealthy/injurious body/organ conditions; such as, acetone gas for diabetes, trimethylamine for uremic patients and ammonia gas for renal disease. Hence, the VOCs in the human breath can be potentially applied as disease-specific biomarkers for non-invasive early detection or monitoring of a variety of diseases.

SUMMARY

Embodiments described herein relate to a sensor for detecting, identifying, quantifying, and/or determining the amount or level of volatile organic compounds (VOCs) in a sample, and particularly relates to a biosensor for detecting, identifying, quantifying, and/or determining the amount or level of VOCs, such as acetone, in a biological or bodily sample, such as breath, blood, and other physiological fluids.

The sensor includes a substrate, a working electrode formed on a surface of the substrate, a counter electrode formed on the surface of the substrate, a dielectric layer covering a portion of the working electrode and counter electrode and defining an aperture exposing other portions of the working electrode and counter electrode.

A membrane, which facilitates an electrochemical reduction reaction with VOCs, covers exposed portions of the working electrode and counter electrode. In some embodiments, the membrane is semi-permeable to allow passage of VOCs, such as acetone, through the film and inhibit passage of anions that interfere with VOC detection.

The membrane includes a polyelectrolyte film, a glycol, an acid for contributing protons, and a metal oxide. The polyelectrolyte film can include a perfluorosulfonic acid polymer. The perfluorosulfonic acid polymer can include nafion or a nafion blend. The glycol can include diethylene glycol, ethylene glycol or another glycol that can maintain or enhance the stability of the membrane.

The metal oxide can include any metal oxide that enhances the hydration and conductivity of the membrane. In one example, the metal oxide can be tungsten trioxide.

The acid acts as a proton source for the electrochemical reduction reaction with the VOCs. In some embodiments, the acid can be sulfuric acid that is provided at a concentration of about 0.1M to about 1M.

In still other embodiments, the working electrode and the counter electrode include metalized films. For example, the working electrode and counter electrode can independently comprise gold, platinum, palladium, silver, carbon, alloys thereof, and composites thereof. The metalized films can be provided on the surface of the substrate by sputtering or coating the films on the surface and then laser ablating the films to form the working electrode and counter electrode.

In some embodiments, the VOCs can be organic chemical compounds that can be associated with and/or can affect human or animal health. The VOCs can be present in the biological or bodily sample and be indicative of the health of a subject and/or the progression of a disease or pathology. Examples of VOCs that may be detected include ethanoic, butanoic and pentanoic acids, benzaldehyde, ethanal, ethylene glycol, carbon disulfide, dimethyldisulfide, acetone, 2-butanone, 2,3-butanedione, 6-methyl-5-hepten-2-one, indole, and 4-methylphenol. In one example, the VOC can be acetone that is detected in a biological sample from the subject, such as breath, and be used to measure the progression of a disease or disorder, such as chronic kidney disease and/or diabetes.

In other embodiments, the sensor can include a reference electrode on the surface of the substrate. The dielectric can cover a portion of the reference electrode. The sensor can also include a measuring device for applying voltage potentials to the working electrode and counter electrode and measuring the current flow between the working electrode and counter electrode to determine the level of the VOC in a sample, such as a biological sample.

DETAILED DESCRIPTION

Unless specifically addressed herein, all terms used have the same meaning as would be understood by those of skilled in the art of the subject matter of the application. The following definitions will provide clarity with respect to the terms used in the specification and claims.

As used herein, the term "quantitative data" or "quantitative level" or "quantitative amount" refers to data, levels, or amounts associated with any dataset components (e.g., markers, clinical indicia,) that can be assigned a numerical value.

As used herein, the term "subject" refers to animal or mammal. Typically, the terms "subject" and "patient" are used herein interchangeably in reference to a human individual.

As used herein, the terms "bodily sample" and "biological sample" refer to a sample that may be obtained from a subject (e.g., a human) or from components (e.g., tissues) of a subject. The sample may be of any biological tissue or fluid with which biomarkers described herein may be assayed. Frequently, the sample will be a "clinical sample", i.e., a sample derived from a patient. Such samples include, but are not limited to, bodily fluids, e.g., urine, blood, plasma, breath, or sera; and archival samples with known diagnosis, treatment and/or outcome history. The term biological sample also encompasses any material derived by processing the biological sample. Processing of the bodily sample may involve one or more of, filtration, distillation, extraction, concentration, inactivation of interfering components, addition of reagents, and the like.

As used herein, the terms "control" or "control sample" refer to one or more biological samples isolated from an individual or group of individuals that are normal (i.e., healthy).

Embodiments described herein relate to a sensor for detecting, identifying, quantifying, and/or determining the amount or level of volatile organic compounds (VOCs), such as acetone, in a sample, and particularly relates to a disposable, and cost-effective biosensor for detecting, identifying, quantifying, and/or determining the amount or level of VOCs in a bodily sample or bodily fluid, such as breath, blood, and other physiological fluids.

The sensors described herein utilize an electrochemical method to reduce the VOCs and thereby generate electrical currents indicative of the concentration of the VOC in a sample, such as a bodily sample.

The sensor can be configured such that it selectively detects a particular VOC in the bodily sample by providing materials covering and/or on the working and/or counter electrode that facilitate the absorption of the particular VOC to the surface of the working electrode and/or the oxidation-reduction of the particular VOC at working electrode surface. For example, the sensor can be configured to selectively detect acetone in bodily sample, such as breath, by proving a membrane, including metal oxides particles (e.g., $WO_3$ nanoparticles), on the surface of the working and counter electrodes that selectively absorb or facilitate the oxidation-reduction reaction with acetone.

The membrane can include a polyelectrolye film the covers or encapsulates portions of a working and counter electrode in a VOC detection region of the sensor. The polyelectrolyte film prevents the substantial diffusion of interfering substances to the electrodes and can include at least one compound that is capable of increasing the rate of electrochemical oxidation-reduction reaction with the particular VOC being detected and provides the detection of the VOC at a lower oxidation potential compared to a sensor that does not include the compound.

The sensor may be used in a variety of contexts. In various embodiments, the sensor can be used to detect VOCs (e.g., acetone) associated with a range of diseases including gastrointestinal disease, chronic liver disease, and pulmonary, localized, and systemic infections. In addition, the sensor can be used to diagnose various metabolic diseases, such as diabetes, obesity or impaired glucose tolerance, and chronic kidney disease.

In some embodiments, the sensor can be used for the detection and monitoring of diabetes, chronic kidney disease, and the staging and monitoring of diabetes and chronic kidney disease progression. The detection and monitoring of diabetes, chronic kidney disease, and the staging and monitoring of diabetes and chronic kidney disease progression can be performed by exposing the sensor to at least one biological sample from the subject, such as exhaled breath, and measuring a signal generated by at least one VOC in sample that is indicative of diabetes and/or chronic kidney disease, such as acetone, thereby providing the diagnosis, staging, or monitoring diabetes and/or chronic kidney disease.

Figure 1:
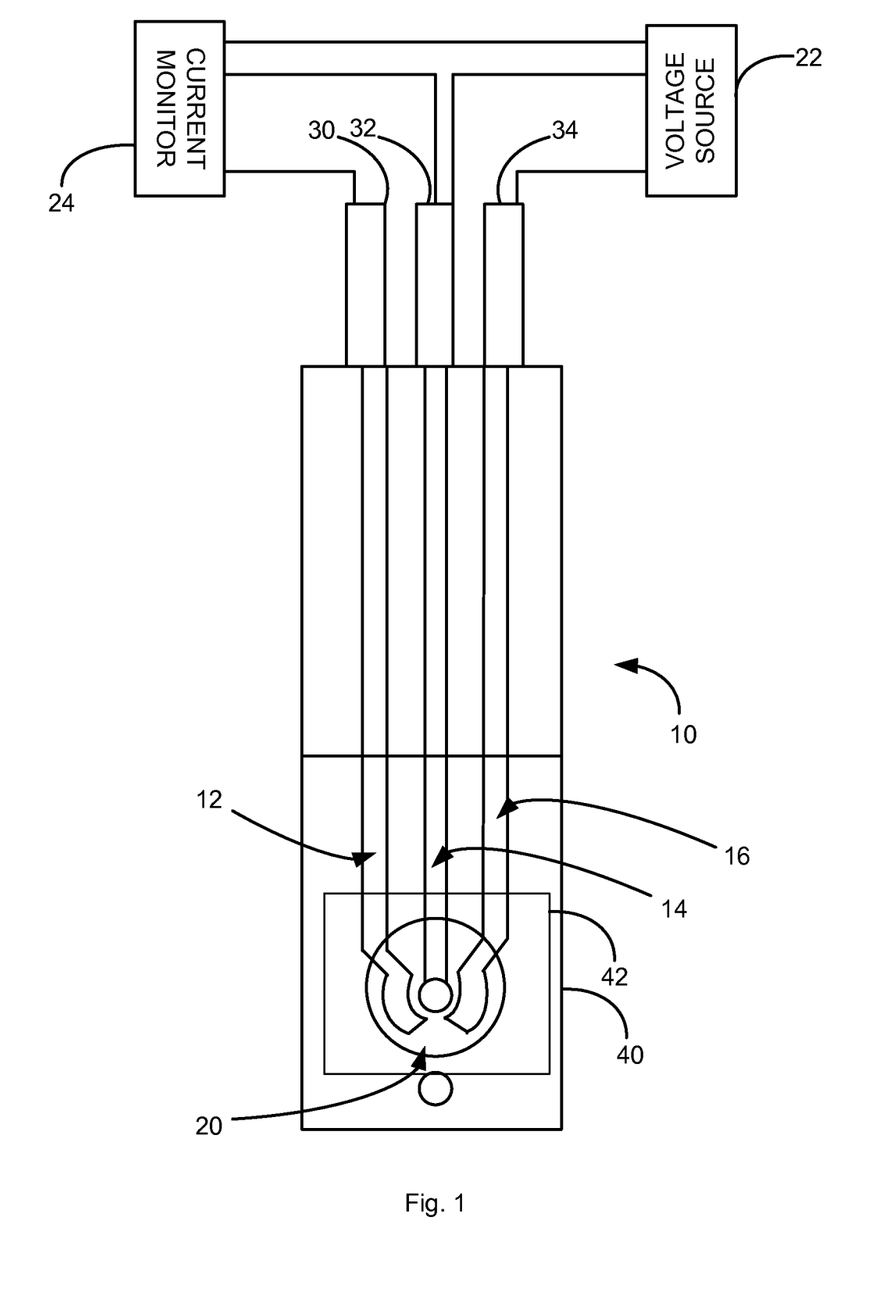
FIG. 1 is a schematic illustration of a biosensor in accordance with an aspect of the application.

FIG. 1 illustrates a sensor 10 in accordance with an embodiment of the application. The sensor 10 is a three-electrode sensor including a counter electrode 12, a working electrode 14, and a reference electrode 16 that are formed on the surface of a substrate. A dielectric layer 40 covers a portion of the working electrode 12, counter electrode 14 and reference electrode 16. The dielectric layer 40 includes an aperture 20 which define a detection region of the working electrode 12, counter electrode 14, reference electrode 16 that is exposed to samples in which the levels of VOCs are detected.

A voltage source 22 is connected to the working and reference electrodes 14, 16. A current measuring device 24 is connected to the working and counter electrodes 14, 12 to measure the current generated by the redox reaction of VOC when a sample or biological sample contacts the detection region 20 of the sensor 10.

The working electrode 14 is the site of the redox reaction of the VOC, and where the charge transfer occurs. The function of the counter electrode 12 is to complete the circuit, allowing charge to flow through the sensor 10. The working electrode 14 and the counter electrode 12 are preferably formed of the same material, although this is not a requirement. Examples of materials that can be used for the working electrode 14 and counter electrode 12 include, but are not limited to, gold, platinum, palladium, silver, carbon, alloys thereof, and composites thereof.

Examples of materials that can be used to form the reference electrode 16 are silver-silver chloride and mercury-mercuric chloride (Calomel). Silver-silver chloride is preferred. The silver can be applied to a substrate in the form of a silver ink, which is commercially available, or can be made using finely dispersed metal particles, solvent, and a binder. Respective silver contact pads 30, 32, and 34 are connected with each of the electrodes 12, 14, and 16. This reference electrode can be thick film printed on the same substrate of the working and counter electrode and also can be used externally.

In some embodiments, the working and counter electrodes 14, 12 can include a layer of particles, such as micro-, meso- or nano-sized catalyst particles of active carbon or porous carbon. The active carbon nanoparticles may be combined with metallic catalyst particles that increase the rate of electrochemical oxidation-reduction reaction with at least one VOC and provide the detection of the at least one VOC at a lower oxidation potential than without the presence of the catalyst particles. In terms of the practical applications, the metallic catalyst particles can shorten the reaction time and lower the applied electrochemical potential for detection of the at least one VOC in the biological sample. Lowering the applied potential often leads to the minimization of electrochemical oxidation or reduction of other species presented, resulting in a minimization of interference caused by the unwanted reaction of the confounding species. As a result, a highly specific biosensor can be obtained and produced.

The metallic catalyst particles can include nano-, meso-, or micro-scale particles of a unary metal (M), a binary metal (M-X), a unary metal oxide (MOy), a binary metal oxide (MOy-XOy), a metal-metal oxide composite material (M-MOy) or a combination of which, wherein y is less than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb. In one embodiment, for example, the metallic catalyst particles may be composed of a unary metal, unary metal oxide binary metal, or binary metal oxide, such as iridium, iridium oxide, platinum, ruthenium, platinum-ruthenium, platinum-nickel, and platinum-gold.

A membrane 42, which facilitates an electrochemical oxidation reduction reaction with VOCs, covers the detection region 20 and exposed portions working electrode, counter electrode, reference electrode. The membrane can include a polyelectrolyte film a glycol, a proton source, and a metal oxide.

The membrane and/or polyelectrolyte film can be selectively or semi-permeable to allow passage of at least one VOC through the film and inhibits passage anions that interfere with detection of the at least one VOC being detected. Other substances may also be permitted to diffuse through the film. Such biologically relevant substances include, but are not limited to, nitrogen, oxygen, carbon monoxide, carbon dioxide, and nitrogen dioxide. These biologically relevant substances generally possess different electric potentials than that of VOCs, such as acetone, and, thus, typically do not interfere with the oxidation of the VOC.

In some embodiments, the polyectrolyte film can be formed from a perfluorosulfonic acid polymer. The perfluorosulfonic acid polymer can be a cation permeable thermoplastic perfluorosulfonic acid polymer that can be solution cast to provide a thin film. An example of a thermoplastic perfluorosulfonic acid polymer, which can be solution cast, is Nafion, which is commercially available from Ion-power Inc. (New Castle, Del.). The use of a cation permeable polymer can also minimize any potential interference by any anion.

In some embodiments, the perfluorosulfonic acid polymer can comprise Nafion or a Nafion blend. Nafion can be blended with other thermoplastic polymers or blends of polymers typically used in forming a polyelectrolyte films. Example of such polymers are sulfonated derivatives of polyphosphazene, poly(ether ketone), polysulfone, polyetetrafluoroethylene, and polyimide.

The glycol can include any glycol that can maintain or enhance the stability of the membrane or the casting of the polyelectrolyte film. In some embodiments, the glycol can be diethylene glycol, ethylene glycol, or another glycol.

The metal oxide can include any metal oxide that enhances the hydration and conductivity of the membrane. In one example, the metal oxide can be tungsten trioxide.

The acid acts as proton source for the electrochemical reduction reaction with the VOCs. In some embodiments, the acid can be sulfuric acid that is provided at a concentration of about 0.1M to about 1M.

The voltage source can apply a voltage potential to the working electrode 14 and reference and/or counter electrode 16, 12, depending on the design of the sensor 10. The current between the working electrode 14 and counter electrode 16 can be measured with a measuring device or meter. Such current is due to the reduction occurring at the working electrode 12 of VOC in the sample that is provided at the detection region.

The amount or level of current measured is proportional to the level or amount of the at least one VOC in the sample. In some embodiments, where the sample is a bodily sample obtained from a subject that has or is suspected of having a condition, pathology, or disorder associated with aberrant VOC levels, once the current level generated by the bodily sample tested with the sensor is determined, the level can be compared to a predetermined value or control value to provide information for diagnosing or monitoring of the condition, pathology, or disorder in a subject. For example, the current level can be compared to a predetermined value or control value to determine if a subject has an infection. An increased current level compared to a predetermined value or control value can be indicative of the subject having, for example, chronic kidney disease; whereas similar or decreased current level compared to a predetermined value or control value can be indicative of the absence of chronic kidney disease of the subject The current level generated by the bodily sample obtained from the subject can be compared to a current level of a bodily sample previously obtained from the subject, such as prior to administration of a therapeutic. Accordingly, the methods described herein can be used to measure the efficacy of a therapeutic regimen for the treatment of a condition, pathology, or disorder associated with VOC levels in a subject by comparing the current level obtained before and after a therapeutic regimen. Additionally, the methods described herein can be used to measure the progression of a condition, pathology, or disorder associated with VOC levels in a subject by comparing the current level in a bodily sample obtained over a given time period, such as days, weeks, months, or years.

The current level generated by a bodily sample of the subject may also be compared to a predetermined value or control value to provide information for determining the severity or aggressiveness of a condition, pathology, or disorder associated with aberrant VOC levels in the subject. A predetermined value or control value can be based upon the current level in comparable samples obtained from a healthy or normal subject or the general population or from a select population of control subjects.

The predetermined value can take a variety of forms. The predetermined value can be a single cut-off value, such as a median or mean. The predetermined value can be established based upon comparative groups such as where the current level in one defined group is double the current level in another defined group. The predetermined value can be a range, for example, where the general subject population is divided equally (or unequally) into groups, or into quadrants, the lowest quadrant being subjects with the lowest current level, the highest quadrant being individuals with the highest current level. In an exemplary embodiment, two cutoff values are selected to minimize the rate of false positive and negative results.

In other embodiments, a detection system can include a plurality of sensors that can be provided in an array on a surface of a substrate. The sensor array can be configured to detect VOC concentration changes as well as the concentrations of other analytes indicative of a disease in a biological sample of a subject. The sensor array can include a plurality biosensors arranged in a plurality of rows and a plurality of columns. Each biosensor comprises on a working electrode and a counter electrode. The working electrode can be modified or functionalized to detect at least one of the VOC analytes of interest. The sensors of the array can be configured to provide at least one output signal representing the presence and/or concentration of a VOC analyte in the sample. For each column of the plurality of columns or for each row of the plurality of rows, the array further comprises column or row circuitry configured to provide voltage potentials to respective sensors in the column or row. Each sensor in the row or column can potentially detect a different VOC analyte and/or biased to detect different analytes.

In some embodiments, the detection system comprising a plurality of sensors can further include a processing unit comprising a pattern recognition analyzer, wherein the pattern recognition analyzer receives sensor output signals and analyses them by various pattern analysis algorithms to produce an output signature. By comparing an unknown signature with a database of stored or known signatures, VOCs indicative of a specific disease can be identified. The analyzer utilizes learning and pattern recognition algorithms comprising artificial neural networks, support vector machine (SVM), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods such as principal component analysis (PCA), partial least squares (PLS), multiple linear regression (MLR), principal component regression (PCR), discriminant function analysis (DFA) including linear discriminant analysis (LDA), and cluster analysis including nearest neighbor.

In some embodiments, the algorithm used for processing the data is an artificial neural network algorithm. In another exemplary embodiment, the algorithm used for processing the data is support vector machine (SVM).

Support Vector Machine (SVM) performs classification by constructing an N-dimensional hyperplane that optimally separates the data into two categories. SVM models are closely related to neural networks. Using a kernel function, SVM models are alternative training methods for polynomial, radial basis function and multi-layer perceptron classifiers in which the weights of the network are derived by solving a quadratic programming problem with linear constraints, rather than by solving a non-convex, unconstrained minimization problem as in standard neural network training. Using an SVM model with a sigmoid kernel function is equivalent to a two-layer, perceptron neural network.

Using the SVM model, a predictor variable is called an attribute, and a transformed attribute that is used to define the hyperplane is called a feature. The task of choosing the most suitable representation is known as feature selection. A set of features that describes one case (i.e., a row of predictor values) is called a vector. The output of SVM modeling provides the optimal hyperplane that separates clusters of vectors in a manner that affords cases with one category of the target variable on one side of the plane and cases with the other category on the other size of the plane. The vectors near the hyperplane are the support vectors.

Additional algorithms suitable for identifying patterns of VOCs indicative of a specific disease can include, but are not limited to, Fisher linear discriminant analysis (FLDA), soft independent modeling of class analogy (SIMCA), K-nearest neighbors (KNN), neural networks, genetic algorithms, and fuzzy logic algorithms. Each possibility represents a separate embodiment of the present invention. In some embodiments, the Fisher linear discriminant analysis (FLDA) and canonical discriminant analysis (CDA) and combinations thereof are used to compare the output signature and the available data from the database. After analysis is completed, the resulting information can be displayed on a display or transmitted to a host computer.

The present invention further provides a method of diagnosing, staging and monitoring a disease, such kidney disease, diabetes, or liver disease in a subject using the sensor or array of sensors. The sensor or array of sensors is exposed to a test exhaled breath sample and a signal or a plurality of signals each comprising at least one response induced parameter is measured. The obtained signal may be analyzed as is. In accordance with these embodiments, the signal is analyzed by comparing it to the response from a control sample whereby a significantly different response of the test sample as compared the control sample is indicative of the disease or its stage.

Alternatively, the signal may be analyzed using a pattern recognition algorithm. In accordance with these embodiments, the plurality of signals (or plurality of response induced parameters, i.e., features) forms a response pattern. The response pattern is compared to the response pattern obtained from a control sample (which can be stored in a database) whereby a significantly different response pattern of the test sample as compared the control sample is indicative of the disease or its stage.

In particular embodiments, the response induced parameters are selected from the group consisting of steady state normalized response, the time interval for obtaining steady state normalized response, and the time required to reach baseline after removal of the test sample. Each possibility represents a separate embodiment of the present invention.

In exemplary embodiments, the response induced parameters are selected from the group consisting of full non-steady state response at the beginning of the signal, full non-steady state response at the beginning of the signal normalized to baseline, full non-steady state response at the middle of the signal, full non-steady state response at the middle of the signal normalized to baseline, full steady state response, full steady state response normalized to baseline, area under non-steady state response, area under steady state response, the gradient of the response upon exposure to the test sample, the gradient of the response upon removal of the test sample, the time required to reach a certain percentage of the response, such as the time required to reach 10%, 20%, 30%, 40%, 50%, 60%, 70%, 80%, 90% or 100% of the response upon exposure to the test sample, and the time required to reach a certain percentage of the response, such as the time required to reach 100%, 90%, 80%, 70%, 60%, 50%, 40%, 30%, 20% or 10% of the response upon removal of the test sample.

Figure 2:
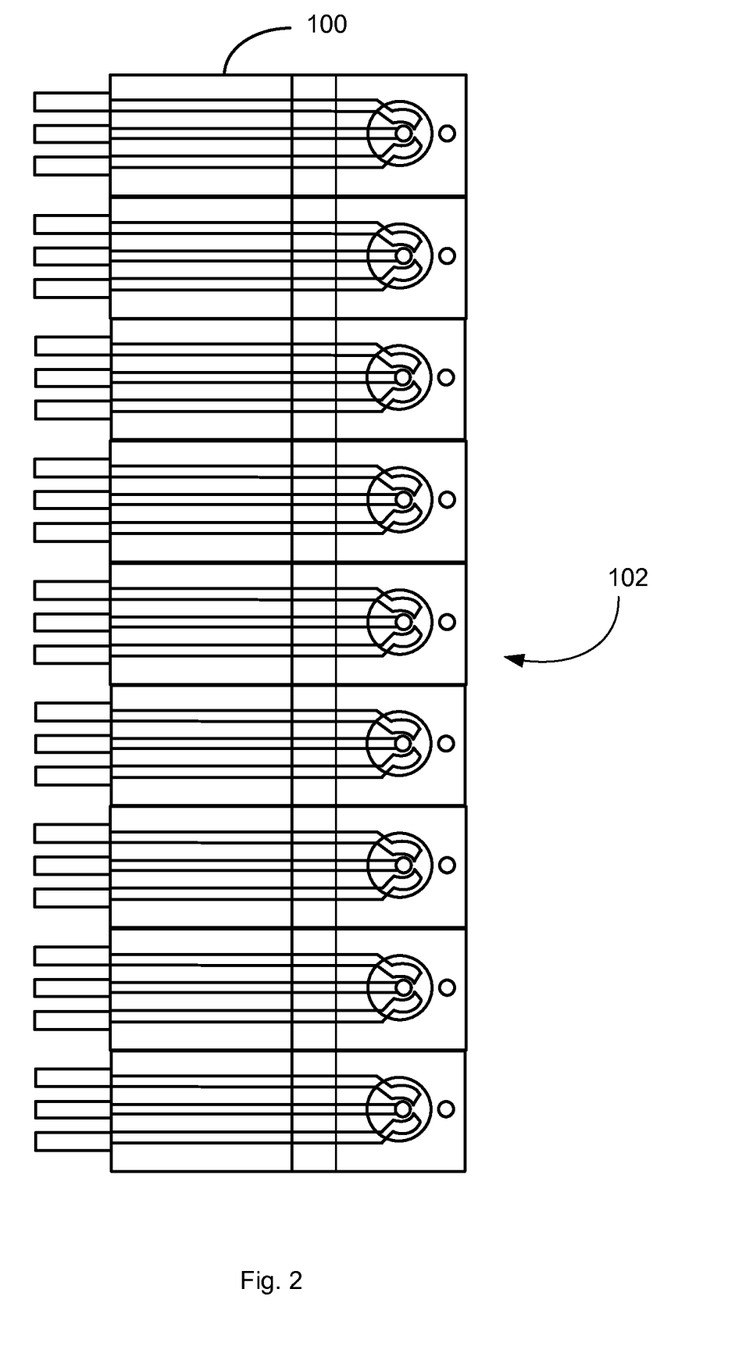
FIG. 2 is a top plan view of an array of biosensors in a row manufactured by a screen-printing process and laser ablation process.

The biosensor illustrated in FIGS. 1 and 2 can be fabricated on a substrate 100 formed from polyester or other electrically non-conductive material, such as other polymeric materials, alumina ($Al_2O_3$), ceramic based materials, glass or a semi-conductive substrate, such as silicon, silicon oxide and other covered substrates. Multiple sensor devices 102 can thus be formed on a common substrate 100 (FIG. 2). As will be appreciated, variations in the geometry and size of the electrodes are contemplated.

The biosensor can be made using a thin film, thick film, and/or ink-jet printing technique, especially for the deposition of multiple electrodes on a substrate. The thin film process can include physical or chemical vapor deposition. Electrochemical sensors and thick film techniques for their fabrication are discussed in U.S. Pat. No. 4,571,292 to C. C. Liu et al., U.S. Pat. No. 4,655,880 to C. C. Liu, and co-pending application U.S. Ser. No. 09/466,865, which are incorporated by reference in their entirety. By way of example, in the case of the carbon electrodes, active carbon is mixed with a binder, deposited like an ink on the substrate, and allowed to dry.

In some embodiments, the working electrode, counter electrode, and reference electrode may be formed using laser ablation, a process which can produce elements with features that are less than one-thousandth of an inch. Laser ablation enables the precise definition of the working electrode, counter electrode, and reference electrode as well as electrical connecting leads and other features, which is required to reduce coefficient of variation and provide accurate measurements. Metalized films, such as Au, Pd, and Pt or any metal having similar electrochemical properties, that can be sputtered or coated on plastic substrates, such as PET or polycarbonate, or other dielectric material, can be irradiated using laser ablation to provide these features.

In one example, a platinum film with a thickness of about 300 to about 2000 A can be deposited by a sputtering technique resulting in very uniform layer that can be laser ablated to form the working and counter electrodes. The counter electrode can use other materials. However, for the simplicity of fabrication, using identical material for both working and counter electrodes will simplify the fabrication process providing the feasibility of producing both electrodes in a single processing step. An Ag/AgCl reference electrode, the insulation layer, and the electrical connecting parts can then be printed using thick-film screen printing technique.

In some embodiments, the overall dimensions of an individual sensors are chosen to be 33.0×8.0 mm². The total width of each individual biosensor is approximately 2.8 mm with a working electrode of 1.0 mm in diameter sufficiently to accommodate up to a 5 µL sample volume. These sizes can be changed as needed.

In some embodiments, particle catalysts can be deposited on the sensor so formed using deposition or screen printing techniques.

In other embodiments, a membrane comprising the polyelectrolyte film can be provided on the sensor so formed. In some embodiments, the membrane that is applied to sensor includes a mixture of Nafion, diethylene glycol, sulfuric acid and tungsten trioxide. In one example, approximately 5 µL of the mixed Nafion, diethylene glycol, sulfuric acid and tungsten trioxide can be placed on top of the sensor, and so that the solution spreads evenly over the whole sensor. The sensor can then be dried either at ambient condition overnight or dried in a vacuumed oven at 80° C. The dried biosensor is then ready for use.

By way of example, in the preliminary testing of this sensor, a small plastic test chamber with gas inlet and outlet is constructed and used. The overall dimensions of the test box are 13.3 cm×5.7 cm×5.7 cm. The dimensions of this chamber are not critical in this evaluation process, and they can be varied. A mass-flow controlled system with two gas inlets are connected to the test box. A gas mixture of acetone in $N_2$ and a pure air are used and controlled producing the required concentration of acetone in the test box. The gas mixture first passes through a glass gas bubbler humidifying the gas prior to feed into the test box. The test gas also can be fed directly into the test chamber without the gas humidifier. The gas mixture with known acetone concentration passes through the test box for two minutes in order to have a fixed, equilibrated nitric oxide concentration in the test box. This two minute of time is not a critical parameter. In this preliminary test, it is sufficient to provide a well defined acetone concentration in the test environment. Then both gas inlet and outlet valves are then closed, and electrochemical measurement is then made. An Electrochemical Workstation (CHI 660 Model A to D, Austin, Tex.) is used in these measurements, and any other electrochemical potentiostat can also be employed. Differential pulse voltammetry (DPV) is employed as the electrochemical analytical technique for this measurement.

Figure 3:
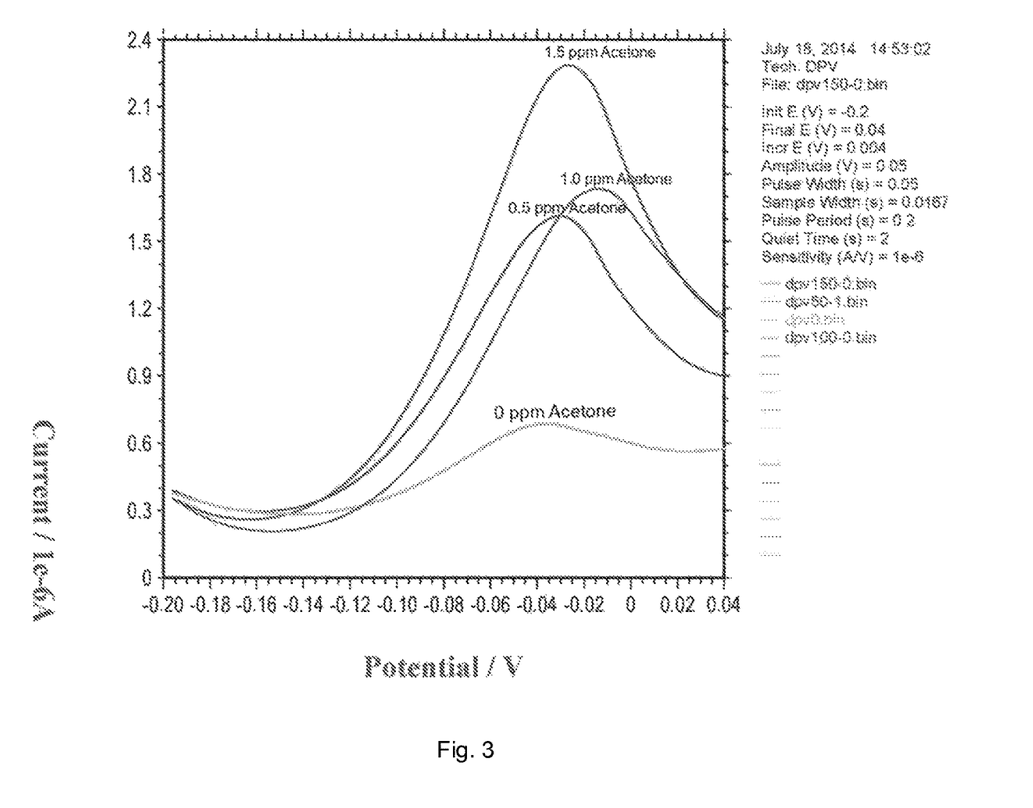
FIG. 3 illustrates a plot showing differential pulse of voltammetry (DPV) measurements over the concentration range of 0-1.5 ppm levels using a biosensor with a platinum working and counter electrode and Ag/AgCl reference electrode in accordance with one embodiment. The legend on the right hand side indicates the DPV measurements.

In order to carry out the detection of acetone in ppm (parts per million) range, a different experimental arrangement is needed. Acetone of 250 ppb level is used. The acetone is then mixed with air further diluting the acetone concentration in 0.1-5 ppm range. The air diluted acetone gas sample is then used to fill a balloon type gas reservoir. The gas from the balloon is then hand-pressed feeding into the test chamber. Differential pulse voltammetric measurement and/or cyclic voltammetric measurements can then be made. It requires about 20 seconds completing one experimental run. This operating time can be adjusted, if needed. FIG. 3 show the typical experimental response to acetone concentration in air in ppm level for platinum electrode (FIG. 3) sensors.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

The invention claimed is:

1. A sensor for the detection of volatile organic compounds (VOCs) comprising:
   a substrate;
   a working electrode formed on a surface of the substrate;
   a counter electrode formed on the surface of the substrate;
   a dielectric layer covering a portion of the working electrode and counter electrode and defining an aperture exposing other portions of the working electrode and counter electrode; and
   a membrane covering the entirety of exposed portions of the working electrode and counter electrode that facilitates an electrochemical oxidation reduction reaction with VOCs, the membrane including a cation permeable thermoplastic perfluorosulfonic acid polymer film, diethylene glycol, an acid for contributing protons, and tungsten trioxide;
   wherein the membrane is semi-permeable to allow passage of a VOC through the membrane and inhibit the passage of anions that interfere with VOC detection.

2. The sensor of claim 1, wherein the VOC detected is acetone.

3. The sensor of claim 1, wherein the working electrode and the counter electrode comprise metalized films.

4. The sensor of claim 1, wherein the working electrode and counter electrode independently comprise gold, platinum, palladium, silver, carbon, alloys thereof, and composites thereof.

5. The sensor of claim 1, the acid comprising sulfuric acid.

6. The sensor of claim 1, the metalized films are provided on the surface of the substrate by sputtering or coating the films on the surface and wherein the working electrode and the counter electrode are formed using laser ablation.

7. The sensor of claim 1, further comprising a reference electrode on the surface of the substrate, the dielectric covering a portion of the reference electrode.

8. The sensor of claim 1, further comprising a measuring device for applying voltage potentials to the working electrode and counter electrode and measuring the current flow between the working electrode and counter electrode.

9. A sensor for detection of acetone in a bodily sample, the sensor comprising:
   a substrate;
   a working electrode formed on a surface of the substrate;
   a counter electrode formed on the surface of the substrate;
   a reference electrode formed on the surface of the substrate;
   a dielectric layer covering a portion of the working electrode, counter electrode, and reference electrode, the dielectric defining an aperture exposing other portions of the working electrode, counter electrode, and reference electrode; and a membrane covering the entirety of exposed portions of the working electrode, counter electrode, and reference electrode that facilitates an electrochemical oxidation reduction reaction with acetone, the membrane including a cation permeable thermoplastic perfluorosulfonic acid polymer film, diethylene glycol, an acid for contributing protons, and a metal oxide comprising tungsten trioxide;

wherein the membrane is semi-permeable to allow passage of acetone through the membrane and inhibit the passage of anions that interfere with acetone detection.

10. The sensor of claim 9, wherein the biological sample is a biological fluid.

11. The sensor of claim 9, wherein the biological fluid is exhaled air, blood, or other physiological fluids.

12. The sensor of claim 9, wherein the working electrode and the counter electrode comprise metalized films.

13. The sensor of claim 9, wherein the working electrode and counter electrode independently comprise gold, platinum, palladium, silver, carbon, alloys thereof, and composites thereof.

14. The sensor of claim 9, the acid comprising sulfuric acid.

15. The sensor of claim 9, the metalized films are provided on the surface of the substrate by sputtering or coating the films on the surface and wherein the working electrode and the counter electrode are formed using laser ablation.

16. A sensor for the detection of volatile organic compounds (VOCs) comprising:
a substrate;
a working electrode formed on a surface of the substrate;
a counter electrode formed on the surface of the substrate;
a dielectric layer covering a portion of the working electrode and counter electrode and defining an aperture exposing other portions of the working electrode and counter electrode; and
a membrane covering the entirety of exposed portions of the working electrode and counter electrode that facilitates an electrochemical oxidation reduction reaction with VOCs, the membrane including a cation permeable thermoplastic perfluorosulfonic acid polymer film, diethylene glycol, sulfuric acid for contributing protons, and tungsten trioxide;
wherein the membrane is semi-permeable to allow passage of a VOC through the membrane and inhibit the passage of anions that interfere with VOC detection.

* * * * *